United States Patent
Kimura et al.

[11] Patent Number: 6,008,315
[45] Date of Patent: Dec. 28, 1999

[54] MANUFACTURING METHOD FOR BISPHENOLS AND A MANUFACTURING METHOD FOR POLYCARBONATE

[75] Inventors: Takato Kimura; Satoru Omori, both of Ichihara, Japan; Ryozo Sato, Murcia, Spain; Tomoaki Shimoda, Ichihara, Japan

[73] Assignee: General Electric Company, Schenectady, N.Y.

[21] Appl. No.: 09/208,651

[22] Filed: Dec. 10, 1998

[30] Foreign Application Priority Data

Dec. 24, 1997 [JP] Japan .................................. 9-355055

[51] Int. Cl.⁶ .................................................. C08G 63/00
[52] U.S. Cl. ............................ 528/176; 528/190; 528/193
[58] Field of Search ..................... 528/176, 190, 528/193

[56] References Cited

U.S. PATENT DOCUMENTS 4,931,146  6/1990  Iimuro et al. .............................. 203/92
5,180,676  1/1993  Ichikawa et al. ......................... 435/383

FOREIGN PATENT DOCUMENTS 63-132850   6/1988   Japan.
2028126    1/1990   Japan.
8325184   12/1996   Japan.

Primary Examiner—Terressa Mosley

[57] ABSTRACT

A phenol and a ketone are reacted to form bisphenol, and the liquid bisphenol obtained or a mixed solution of said solution and a phenol is filtered through a calcined metal filter to obtain bisphenol which makes it possible to efficiently obtain bisphenol which either does not contain fine particulate impurities or contains such impurities only in minute amounts, and a method for manufacturing polycarbonate using bisphenol obtained by this method. The filtration grade of the calcined metal filter should be 1.0 $\mu$m or less. After filtering, the calcined metal filter can be backwashed or chemically washed and then reused. The bisphenol should preferably be bisphenol A.

15 Claims, 2 Drawing Sheets

MANUFACTURING METHOD FOR BISPHENOLS AND A MANUFACTURING METHOD FOR POLYCARBONATE

The present invention concerns a method for manufacturing bisphenols which makes it possible to efficiently obtain bisphenol which either does not contain fine particulate impurities or contains such impurities only in minute amounts and a method for manufacturing polycarbonate using bisphenol obtained by said method.

Bisphenols such as bisphenol A and bisphenol F (which is based on fluorenone, an aromatic ketone) have conventionally been widely used as raw materials for manufacturing polymers such as polycarbonate, epoxy resins, and polyarylate. Among the various polymers obtained in this manner from such bisphenols, as polycarbonate shows outstanding mechanical properties such as impact resistance and also shows outstanding thermal resistance, transparency, etc., it has been used in a broad range of applications, but in recent years, there has been a rapid increase in the demand for optical applications in particular, such as substrate materials for optical disks.

Furthermore, in addition to transparency, polymers used as optical materials must also have various optical characteristics, and it is very important that they not contain $\mu$m-sized fine particulate impurities, which can cause optical scattering in the polymer. For example, fine particulate impurities in optical disk substrates give rise to optical heterogeneity, causing the drawback of noise.

Many of these fine particulate impurities in polymers are present as is in the polymer, originating from polymerization raw materials containing fine particulate impurities. For example, in polycarbonates using bisphenol as a polymerization raw material, fine particulate impurities are usually present in the form of inorganic or organic impurities which contaminate the bisphenol at the time of manufacturing. Specifically, bisphenol is generally obtained by reacting phenols and ketones in the presence of an acidic catalyst, but in cases where hydrochloric acid is used as the acidic catalyst, inorganic impurities such as metal oxides originating from corrosion of the manufacturing equipment may contaminate the bisphenol. Moreover, in cases where strongly-acidic ion-exchange resin catalysts are used, organic impurities such as oligomers eluted from the catalyst may contaminate the bisphenol.

Bisphenols therefore contain fine particles, with bisphenols manufactured in commercial plants generally containing some 500–10,000 fine particles having a diameter of 2 $\mu$m or above per g of bisphenol and the number contained frequently being 1,000 or above, and this content varies widely.

For this reason, when bisphenols are used as raw materials for manufacturing polymers, it is necessary to remove the fine particles from the bisphenol in advance, and such removal is generally carried out by filtration. For example, in Japanese Unexamined Patent Application No. H4-325284, a method is presented in which outstanding results for chemical stability and filtration grade are obtained by using a fluorine resin membrane filter for filtering bisphenol A.

However, in filtering of liquid bisphenols using a fluorine resin membrane filter, there is the drawback that filtering becomes difficult due to the high surface tension of the bisphenols. For this reason, it a complex procedure must be carried out in which a fluorine resin membrane filter is first immersed for several hours in a solvent such as phenol at a temperature of 60–120° C., and the bisphenol is then filtered.

Furthermore, in bisphenol production plants, when operations are begun using bisphenol containing large amounts of fine particles, the filter tends to become clogged, making it necessary to change the filter frequently. Moreover, as fluorine resin membrane filters are difficult to reuse once they become clogged, a new filter must be used, which is uneconomical.

The purpose of the present invention, which was developed in light of the above problems with prior art, is to provide a method for manufacturing bisphenol in which bisphenol containing no $\mu$m-sized fine particles or only minute amounts of such particles can be efficiently obtained and a method for manufacturing polycarbonate using bisphenol obtained by said method.

The method for manufacturing bisphenols of the present invention is characterized in that phenols and ketones are reacted to form bisphenols, and the liquid bisphenols obtained or a mixed solution of said bisphenols and phenols is filtered using a calcined metal filter.

According to a preferred embodiment of the present invention, in manufacturing of bisphenol pellets by the following processes:

(a) a process in which a phenol and a ketone are reacted in the presence of an acidic catalyst to form liquid bisphenol, (b) a process in which catalysts and low-boiling-point substances are removed from the reaction mixture containing the liquid bisphenol formed, (c) a process in which a homogeneous solution of bisphenol with an adjusted concentration is obtained by adding or removing phenol, (d) a process in which the homogeneous solution obtained as described above is cooled and an addition compound of bisphenol and phenol is crystallized to form a slurry, (e) a process in which the slurry is subjected to solid-liquid separation to obtain an addition compound of bisphenol and phenol in the form of a solid, (f) a process in which the solid addition compound obtained as described above is heated and melted to obtain a mixed solution, (g) a process in which the phenol is removed from the aforementioned mixed solution to obtain purified bisphenol, and if necessary, (h) a process in which the purified liquid bisphenol obtained in process (g) above is pelletized, the liquid bisphenol obtained in process (a) above, the homogeneous solution obtained in process (c), the mixed solution of bisphenol and phenol obtained in process (f), the purified liquid bisphenol obtained in process (g), or the molten bisphenol pellets obtained in process (h) are filtered using a calcined metal filter.

Among the above processes, it is preferable to filter the mixed solution of bisphenols and phenols obtained by process (f), the purified liquid bisphenols obtained by process (g) or the molten bisphenol pellets obtained by process (h).

It is preferred that the filtration grade of the aforementioned calcined metal filter is 0.1 $\mu$m or less.

After filtering, the calcined metal filter may be backwashed or chemically washed and then reused.

In the present invention, the bisphenol is preferably bisphenol A.

The method for manufacturing polycarbonate of the present invention uses bisphenol obtained as described above as a reaction raw material.

The following will be a specific explanation of the method for manufacturing bisphenols of the present invention.

In the method for manufacturing bisphenols of the present invention, phenols and ketones are reacted to form bisphenols, and the liquid bisphenol obtained or a mixed solution of said bisphenol and phenols is filtered using a calcined metal filter.

Figure 1:
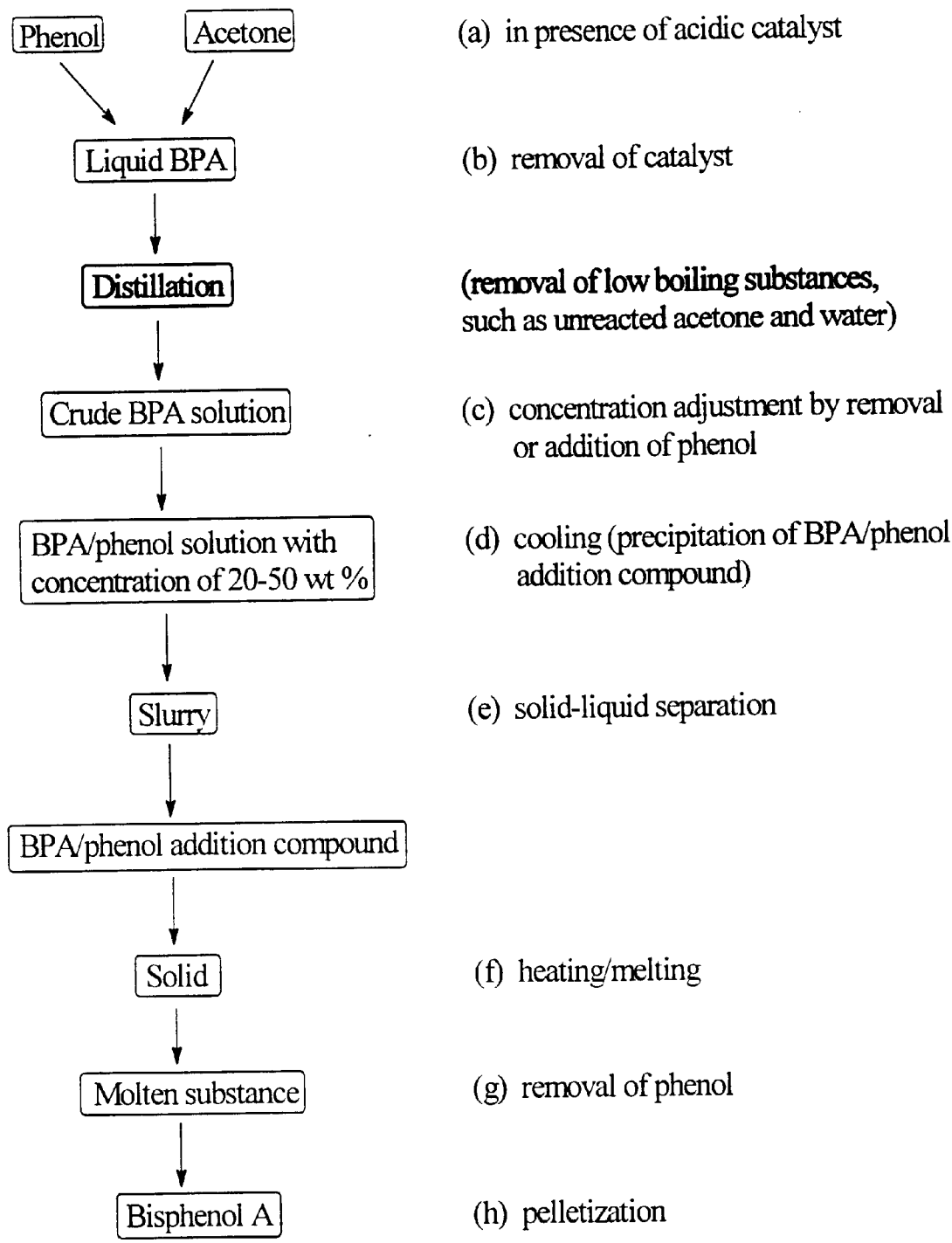
FIG. 1 is a schematic process flow diagram of a preferred method for manufacturing bisphenols according to the present invention.

Specifically, in the method in which bisphenol formed by reacting phenols and ketones according to processes (a)–(h) is made into an addition compound with phenol and the phenol is then removed to manufacture bisphenol, the liquid bisphenol or mixed solution of bisphenol and phenol should preferably be filtered. A specific example of this preferred embodiment is explained with reference to the process flow chart shown in FIG. 1.

Process (a)

In the present invention, phenols and ketones are first reacted to form liquid bisphenols.

In the present invention, for example, the bisphenol obtained by reacting phenols and ketones may have the formula below:

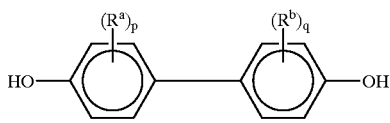

in the formula, $R^a$ and $R^b$ are halogens or monovalent hydrocarbon groups, and they may be the same or different, p and q are integers from 0 to 4, X is

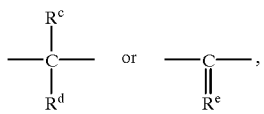

$R^c$ and $R^d$ are hydrogen atoms or monovalent hydrocarbon groups or a ring structure may be formed by $R^c$ and $R^d$, and $R^e$ is a divalent hydrocarbon group.

Specific examples of the bisphenol of formula above include bis(hydroxyaryl)alkanes such as:

1,1-bis(4-hydroxyphenyl)methane,
1,1-bis(4-hydroxyphenyl)ethane,
2,2-bis(4-hydroxyphenyl)propane (referred to in the following as bisphenol A),
2,2-bis(4-hydroxyphenyl)butane,
2,2-bis(4-hydroxyphenyl)octane,
1,1-bis(4-hydroxyphenyl)propane,
1,1-bis(4-hydroxyphenyl)n-butane,
bis(4-hydroxyphenyl)phenylmethane,
2,2-bis(4-hydroxy-1-methylphenyl)propane,
1,1-bis(4-hydroxy-t-butylphenyl)propane,
and 2,2-bis(4-hydroxy-3-bromophenyl)propane,
and bis(hydroxyaryl)cycloalkanes such as
1,1-bis(4-hydroxyphenyl)cyclopentane and
1,1-bis(4-hydroxyphenyl)cyclohexane.

Moreover, in the present invention, bisphenol may be manufactured in such a manner that in the above formula, X is —O—, —S—, —SO—, or —SO$_2$—, with examples of compounds that can be manufactured including bis(hydroxyaryl) ethers such as:

4,4'-dihydroxydiphenyl ether and
4,4'-dihydroxy-3,3'-dimethylphenyl ether,
bis(hydroxydiaryl) sulfides such as:
4,4'-dihydroxydiphenyl sulfide and
4,4'-dihydroxy-3,3'-dimethyldiphenyl sulfide,
bis(hydroxydiaryl) sulfoxides such as:
4,4'-dihydroxydiphenyl sulfoxide and
4,4'-dihydroxy-3,3'-dimethyldiphenyl sulfoxide,
and bis(hydroxydiaryl) sulfones such as:
4,4'-dihydroxydiphenyl sulfone and
4,4'-dihydroxy-3,3'-dimethyldiphenyl sulfone.

Among these substances, manufacturing of bisphenol A is particularly preferred.

Bisphenols such as those described above may be obtained by a commonly-known bisphenol synthesis method in which phenols and ketones are condensed in the presence of an acidic catalyst. Phenols having a structure in which there is not a bond with X in the above formula may be used. Moreover, if the above bisphenols can be obtained, one may also carry out condensation of phenols with formaldehyde, sulfonic acids, etc.

The following is an explanation of manufacturing of bisphenol A (abbreviated in the following as BPA), mainly by dehydration-condensation of phenol and acetone.

Phenol is ordinarily used in an excess amount with respect to the acetone, with the molar ratio of phenol to acetone (phenol/acetone) ordinarily being about 3/30, and preferably about 5/20.

Any commonly-known acidic ion-exchange resin catalyst may be used as the acidic catalyst, and there are no particular restrictions on this catalyst, but ordinarily, a sulfonic acid-type cation-exchange resin having a degree of crosslinking in a gel mold of from about 1 to about 8%, and preferably from about 2 to about 6%, should preferably be used. Furthermore, mineral acid catalysts such as hydrochloric acid and sulfuric acid may also be used.

The reaction of phenol and acetone is ordinarily carried out at a temperature of from about 30 to about 100° C., and preferably of from about 50 to about 90° C., at a pressure ranging from normal pressure to about 5 kg/cm$^2$ G.

In the reaction of the above phenol and acetone, one ordinarily obtains a liquid reaction mixture containing, in addition to bisphenol A, reaction byproducts such as unreacted phenol, unreacted acetone, and water produced as a byproduct.

Process (b)

Catalysts and low-boiling-point substances are removed from the reaction mixture containing liquid bisphenol obtained as described above.

In cases where a mineral acid is used as the above reaction catalyst, prior to removing the low-boiling-point substances from the reaction mixture by distillation, a process for removing the catalyst such as washing with water is carried out. In reactions using a fixed-bed reactor filled with an ion-exchange resin catalyst, as a reaction mixture is obtained which does not contain the catalyst, processing to remove the catalyst is not carried out.

Distillation of the reaction mixture is ordinarily carried out at from about 50 to about 300 mmHg and from about 70 to about 130° C. In this reduced-pressure distillation, together with low-boiling-point substances such as acetone and water, a portion of the phenol is also removed by azeotropy.

Process (c)

A homogeneous bisphenol solution with an adjusted concentration is obtained by the addition or removal of phenols.

Among such phenols, phenol is preferred, and it is preferable, for example, to produce an addition compound of bisphenol A and phenol.

In order to efficiently crystallize the addition compound of bisphenol A and phenol, a homogeneous solution of bisphenol A and phenol should be formed, and the concentration of bisphenol A in this homogeneous solution should be from about 20 to about 50% by weight, and preferably from about 30 to about 45% by weight. This homogeneous solution may be composed of the aforementioned addition compound or of a mixture of this addition compound and phenol.

Process (d)

The homogeneous solution obtained as described above is cooled. and an addition compound of bisphenol and phenol is crystallized to form a slurry.

A homogeneous solution of bisphenol and phenol should preferably be cooled to from about 35 to about 60° C., and cooling should preferably be carried out using an external heat exchanger or by heat extraction at reduced pressure.

Process (e)

The slurry obtained as described above is subjected to solid-liquid separation, and an addition compound of bisphenol and phenol is obtained.

Solid-liquid separation of the slurry may be carried out by methods such as centrifugation and vacuum filtration. By means of this solid-liquid separation, the crystals of the addition product of bisphenol and phenol are separated from the mother liquor, which contains reaction byproducts, etc. The separated addition compound (wet cake) may also be washed with phenol, etc.

Process (f)

The solid addition product obtained as described above is heated and melted.

Addition product crystals separated as described above, e.g., an addition product of bisphenol A and phenol, is ordinarily heated and melted at from about 100 to about 160° C. to obtain a mixed solution (molten mixture).

Process (g)

Phenol is removed from the aforementioned mixed solution (molten mixture) to obtain purified liquid bisphenol. The phenol is removed from the mixed solution by vacuum distillation, etc., to recover liquid bisphenol. In removing the phenol by distillation, vacuum distillation is carried out at a pressure of from about 10 to about 100 mm Hg and a distillation temperature of from about 150 to about 190° C. This process is carried out at a temperature which is at least about 10° C. above the melting point of the mixture of bisphenol A and phenol in the distillation tower.

In process (g), it is also possible to remove the phenol present in the bisphenol by steam stripping, etc., using the methods presented in documents such as Japanese Unexamined Patent Applications H2-28126 and S63-132850.

Process (h)

In process (g) above for manufacturing bisphenol, liquid (molten) purified bisphenol is obtained. In the present invention, this bisphenol may be used in the polycarbonate manufacturing process as is in liquid form, but bisphenol which is not continuously fed into the polymer manufacturing process is ordinarily cooled and pelletized.

Pelletization of the bisphenol is carried out by methods such as atomization, dripping, or spraying of the liquid bisphenol obtained in process (g) above using a spray dryer, etc. to obtain drops of liquid, and these are then cooled and solidified using nitrogen, air, etc.

In the present invention, it is preferable to manufacture the bisphenol by continuously carrying out the above processes (a)–(g), and if needed, (h).

Filtration

In the present invention, in manufacturing the bisphenol according to the process described above, liquid bisphenol obtained in a reaction or a mixed solution of said bisphenol and phenol is filtered to remove minute particles. Specifically, any substance among the liquid bisphenol obtained in process (a) above, the homogeneous solution obtained in process (c), the mixed solution of bisphenol and phenol obtained in process (f), the liquid purified bisphenol obtained in process (g), or the molten bisphenol pellets obtained in process (h) may be filtered. Among these substances, it is preferable to filter the mixed solution of bisphenol and phenol obtained in process (f), the liquid bisphenol obtained in process (g), or the molten bisphenol pellets obtained in process (h).

This filtration is carried out using a calcined metal filter.

Filters are generally classified based on their entrapment structure into the depth type, in which solid matter such as particles is trapped after adhering to pores in the filter, and the screen type, in which solid material is trapped by a sieve on the surface of the filter, and the calcined metal filter used in the present invention can be classified as the ordinary screen type.

The material used in calcined metal filters may be any metal which does not undergo separation or corrosion, with examples including nickel, stainless steel, and nickel alloys such as Hastelloy (commercial name), which are readily available commercially.

The filtration grade (pore diameter) of the calcined metal filter used in the present invention varies depending on factors such as the diameter and number of fine particles contained in the liquid to be processed and the pressure drop of the filter, but it is preferably about 5 $\mu$m or less, and from the standpoint of improving the fine particle removal ratio, a diameter of about 1.0 $\mu$m or less is more preferred. Moreover, in cases where it is necessary to remove particles having a diameter of about 2 $\mu$m or less, it is preferable to use a filter having a filtration grade of about 0.5 $\mu$m, or even more preferably about 0.2 $\mu$m.

The calcined metal filter of the present invention has a high filtration grade (small pore diameter) and can be reused.

An example of such a calcined metal filter is the Porous Filter (commercial name) marketed by Mott Co.

Filtration varies according to factors such as the viscosity of the liquid to be processed, but the liquid is ordinarily passed through with a flow volume of from about 0.2 to about 0.5 gallons/min. per $ft^2$ of the filter.

The above calcined metal filter shows a high filtration grade, outstanding heat resistance, and does not have the problems of contamination with fine particulate impurities due to separation of the filter materials, elution of the binder, etc. Moreover, even in the case of liquid bisphenol having a high surface tension, there is no need for pretreatment such as solvent immersion treatment. The filtration process can therefore be simplified. Moreover, as will be mentioned below, calcined metal filters can be regenerated and reused. Furthermore, as mentioned above, fluorine resin filters require pretreatment such as immersion in a solvent prior to filtration of the bisphenol, and they cannot be said to have sufficient heat resistance to withstand the processing temperature of the molten bisphenol, which is ordinarily on the order of about 185° C. They also cannot be regenerated and reused.

Filtration using this type of calcined metal filter is especially effective at the beginning of plant operation, when many fine particles are contained in the system and contamination tends to occur readily. Moreover, in cases where the number of fine particles is high, it is also effective to carry out prefiltering with a coarse depth-type filter prior to filtering with the calcined metal filter. This makes it possible to reduce the frequency of washing of the calcined metal filter.

In the present invention, when the filter becomes clogged and its entrapment efficiency decreases, its functions can be restored and it can be reused by means of backwashing or chemical washing. Regeneration of the filter makes it possible to increase differential pressure in an inexpensive manner.

Specifically, backwashing of the filter is carried out by stopping the supply of the liquid to be treated to the filter and causing an organic solvent such as distillation-purified phenol to flow through the filter in the opposite direction to the flow of the liquid to be processed, thus washing the filter. This flow of organic solvent should take place under conditions which make it possible to remove the fine particles clogging the filter, and it is usually carried out with a flow volume of from about 0.2 to about 0.5 gallons/min.·ft$^2$ for from about 0.5 to about 24 hours.

Moreover, in chemical washing of the filter, one should preferably use a combination of an acidic aqueous solution of hydrochloric acid, nitric acid, phosphoric acid, etc., or an alkaline aqueous solution such as sodium hydroxide or potassium hydroxide combined with a surfactant as a washing solution. Specific examples are Oakite 31 and Oakite 32 (commercial names, manufactured by Oakite Co.).

A filter regenerated in this manner exhibits performance which is virtually identical to that of a new filter.

By means of the method for manufacturing bisphenol of the present invention, as one can obtain bisphenol which either does not contain $\mu$m-sized fine particles or contains them only in minute amounts, it allows the filtration process to be simplified, and it makes it possible to regenerate and reuse the filter this process, this allows bisphenol to be obtained with a high degree of productivity. The bisphenol obtained in the present invention is particularly well-suited as a raw material for manufacturing polycarbonate for optical disks.

Manufacturing of Polycarbonate

In the present invention, polycarbonate is manufactured using the bisphenol obtained as described above as a reaction raw material. There are no particular restrictions on this method for manufacturing polycarbonate, other than the use of the aforementioned bisphenol, and for example, one may use the interfacial method or the melt polycondensation method (transesterification method), but one should preferably use melt polycondensation, which does not involve the use of poisonous substances such as phosgene or methylene chloride.

In the following, we will describe a method for manufacturing polycarbonate by melt polycondensation of a bisphenol and a carbonic diester as a preferred embodiment of the invention.

In the present invention, the bisphenol manufacturing process and polycarbonate manufacturing process may be carried out continuously. For example, the liquid bisphenol obtained in process (g) above and filtered as described above may be fed into the polycarbonate manufacturing process as is without being pelletized. Alternatively, pelletized bisphenol may be melted, filtered, and then fed into the polycarbonate manufacturing process.

Specific examples of carbonic diesters include diphenylcarbonate, ditolylcarbonate, bis(chlorophenyl) carbonate, m-cresylcarbonate, dinaphthylcarbonate, bis (diphenyl)carbonate, diethylcarbonate, dimethylcarbonate, dibutylcarbonate, and dicyclohexylcarbonate, and these substances may also be used in combinations of two or more. Among these substances, diphenylcarbonate is particularly preferred.

The carbonic diester used in the present invention may include a dicarboxylic acid or dicarboxylic ester. Specifically, the carbonic diester should contain a dicarboxylic acid or dicarboxylic ester in an amount of about 50 m % or less, and preferably about 30 m % or less.

Examples of this dicarboxylic acid or dicarboxylic ester include:

aromatic dicarboxylic acids such as terephthalic acid, isophthalic acid, diphenyl terephthalate, or diphenyl isophthalate;

aliphatic dicarboxylic acids such as succinic acid, glutaric acid, adipic acid, pimelic acid, suberic acid, azelaic acid, sebacic acid, decanedioic acid, dodecanedioic acid, diphenyl sebacate, diphenyl decanedioate, or diphenyl dodecanedioate;

and aliphatic dicarboxylic acids such as dichloropropane dicarboxylic acid, 1,2-cyclopropane dicarboxylic acid, 1,3-cyclobutane dicarboxylic acid, 1,2-cyclopentane dicarboxylic acid, 1,3-cyclopentane dicarboxylic acid, 1,2-cyclohexane dicarboxylic acid, 1,3-cyclohexane dicarboxylic acid, 1,4-cyclohexane dicarboxylic acid, diphenylcyclopropane dicarbonate, 1,2-diphenylcyclobutane dicarbonate, 1,3-diphenylcyclobutane dicarbonate, 1,2-diphenylcyclopentane dicarbonate, 1,3-diphenylcyclopentane dicarbonate, 1,2-diphenyldicyclohexane dicarbonate, 1,3-diphenylcyclohexane dicarbonate, or 1,4-diphenylcyclohexane dicarbonate. The carbonic diesters may contain two or more of these dicarboxylic acids or dicarboxylic esters.

In the present invention, in polycondensation of the carbonic acid diester and bisphenol as described above, one should ordinarily use from about 1.0 to about 1.30 moles of the carbonic diester for each mole of the bisphenol, with an amount of from about 1.01 to about 1.20 moles being particularly preferred.

Moreover, in manufacturing polycarbonate by the method of the present invention, together with the aforementioned bisphenol and carbonic diester, a multifunctional compound having three or more functional groups per molecule may also be used. A compound having a phenolic hydroxyl group or a carboxyl group should preferably be used as this multifunctional compound, with compounds containing three phenolic hydroxyl groups being particularly preferred. Specific examples of the preferred compound include 1,1, 1-tris(4-hydroxyphenyl)ethane, 2,2',2"-tris(4-hydroxyphenyl)diisopropyl benzene, α-methyl-α,α',α"-tris (4-hydroxyphenyl)-1,4-diethylbenzene, α,α',α"-tris(4-hydroxyphenyl)-1,3,5-triisopropylbenzene, phloroglucinol, 4,6-dimethyl-2,4-6-tri(4-hydroxyphenyl)-heptane-2, 1,3,5-tri(4-hydroxyphenyl)benzene, 2,2-bis-[4,4-(4,4'-dihydroxyphenyl)-cyclohexyl]-propane, trimellitic acid, 1,3, 5-benzene tricarboxylic acid, and pyromellitic acid.

Among these, the use of 1,1,1-tris(4-hydroxyphenyl) ethane or α,α',α"-tris(4-hydroxyphenyl)-1,3,5-triisopropylbenzene, etc., is particularly preferred.

The multifunctional compound should preferably be present in the amount of about 0.03 moles or less with respect to 1 mole of the bisphenol, and more preferably in the amount of from about 0.001 to about 0.02 moles, with an amount of from about 0.011 to about 0.01 moles being particularly preferred.

In manufacturing the polycarbonate, the above-mentioned bisphenol and carbonic diester should be used in solid form, or they may be directly supplied from these manufacturing devices in molten form.

As a catalyst for melt polycondensation of the aforementioned bisphenol and carbonic diester, one may use (a) an alkali metal compound and/or alkaline earth metal compound (sometimes abbreviated in the following as "an alkali(ne earth) metal compound"). Examples of such alkali (ne earth) metal compounds include organic acid salts, inorganic acid salts, oxides, hydroxides, hydrides, or alcoholates of alkali metals or alkaline earth metals.

Specific examples of alkali metal compounds include sodium hydroxide, potassium hydroxide, lithium hydroxide, sodium hydrogencarbonate, potassium hydrogencarbonate, lithium hydrogencarbonate, sodium carbonate, potassium carbonate, lithium carbonate, sodium acetate, potassium acetate, lithium acetate, sodium stearate, potassium stearate, lithium stearate, sodium boron hydride, lithium boron hydride, sodium boron phenylate, sodium benzoate, potassium benzoate, lithium benzoate, disodium hydrogenphosphate, dipotassium hydrogenphosphate, dilithium hydrogenphosphate, disodium salts, dipotassium salts, and dilithium salts of bisphenol A, and sodium salts, potassium salts, and lithium salts of phenol, etc., and specific examples of alkaline earth metal compounds include calcium hydroxide, barium hydroxide, magnesium hydroxide, strontium hydroxide, calcium hydrogencarbonate, barium hydrogencarbonate, magnesium hydrogencarbonate, strontium hydrogencarbonate, calcium carbonate, barium carbonate, magnesium carbonate, strontium carbonate, calcium acetate, barium acetate, magnesium acetate, strontium acetate, and strontium stearate, etc. These compounds may be used in combinations of two or more.

In the present invention, this (a) alkali(ne earth) metal compound should be used in the amount of from about $5 \times 10^{-8}$ to about $2 \times 10^{-6}$ moles with respect to 1 mole of the bisphenol, with from about $1 \times 10^{-7}$ to about $2.5 \times 10^{-6}$ moles being preferred, and the amount of from about $1 \times 10^{-7}$ to about $1.2 \times 10^{-6}$ moles being particularly preferable.

The aforementioned alkali(ne earth) metal compounds should preferably be used in a solution, such as an aqueous solution, a solution of alcohols such as methanol or ethanol, or a phenol solution of an alkali(ne earth) metal compound. Furthermore, bisphenols containing the above alkali(ne earth) metal compounds may also be used.

In the present invention, one should preferably use a combination of the above (a) alkali(ne earth) metal compound and (b) a basic compound.

An example of this (b) basic compound is a nitrogen-containing basic compound which decomposes readily or is volatile at high temperatures, with specific examples including the compounds below.

Ammonium hydroxides having alkyl, aryl, and aralkyl groups such as tetramethylammonium hydroxide (Me$_4$NOH), tetraethylammonium hydroxide (Et$_4$NOH), tetrabutylammonium hydroxide (Bu$_4$NOH), and trimethylbenzylammonium hydroxide (ø—CH$_2$(Me)$_3$NOH), etc., tertiary amines such as trimethylamine, triethylamine, dimethylbenzylamine, triphenylamine, trioctylamine, tridodecylamine, and trioctadecylamine, secondary amines indicated by the formula R$_2$NH (in the formula, R indicates an alkyl group such as methyl or ethyl or an aryl group such as phenyl or toluyl), primary amines indicated by the formula RNH$_2$ (in the formula, R has the same meaning as indicated above), pyridines such as 4-dimethylaminopyridine, 4-diethyl aminopyridine, and 4-pyrrolidinopyridine, imidazoles such as 2-methylimidazole and 2-phenylimidazole, or basic salts such as ammonia, tetramethylammonium borohydride (Me$_4$NBH$_4$), tetrabutylammonium borohydride (Bu$_4$NBH$_4$), tetrabutylammonium tetraphenyl borate (Bu$_4$NB(Ph)$_4$), and tetramethylammonium tetraphenyl borate (Me$_4$NB(Ph)$_4$).

Of these substances, tetraalkyl ammonium hydroxides, particularly tetraalkylammonium hydroxides for electronic use which have a low content of metal impurities, are particularly preferable.

The aforementioned (b) nitrogen-containing basic compound should be included in the amount of from about $1 \times 10^{-6}$ to about $1 \times 10^{-1}$ moles, or preferably from about $1 \times 10^{-5}$ to about $1 \times 10^{-2}$ moles, with respect to 1 mole of the bisphenol.

Moreover, (c) a boric acid compound may be used as a catalyst.

Examples of this type of (c) boric acid compound include boric acid and boric acid esters.

As an example of a boric acid ester, one can mention a boric acid ester having the following general formula.

$$B(OR)_n(OH)_{3-n}$$

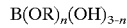

In the formula, R indicates an alkyl group such as methyl or ethyl or an aryl group such as phenyl, and n is the integer 1, 2, or 3.

Specific examples of this boric acid ester include trimethylborate, triethylborate, tributylborate, trihexylborate, triheptylborate, triphenylborate, tritolylborate, and trinaphthylborate.

The (c) boric acid or boric acid ester used as a catalyst may be used in the amount of from about $1 \times 10^{-8}$ to about $1 \times 10^{-1}$ moles, and preferably from about $1 \times 10^{-7}$ to about $1 \times 10^{-2}$ moles, with respect to 1 mole of the aromatic dihydroxy compound, with the amount of from about $1 \times 10^{-6}$ to about $1 \times 10^{-4}$ moles being particularly preferred.

In the present invention, the melt polycondensation catalyst should preferably be a combination of (a) an alkali(ne earth) metal compound together with (b) a nitrogen-containing basic compound, or a combination of (a) an alkali metal compound and/or alkaline earth metal compound, (b) a nitrogen-containing basic compound, and (c) a boric acid or boric acid ester.

When one uses a combination of (a) an alkali(ne earth) metal compound and (b) a nitrogen-containing basic compound in the aforementioned amounts as a catalyst, one can carry out melt polycondensation at a sufficiently rapid rate and obtain a high-molecular-weight polycarbonate with a high degree of polymerization activity, achieving an advantageous result.

The melt polycondensation reaction between the aromatic dihydroxy compound and the carbonic acid diester in the presence of a catalyst may be carried out under conditions identical to those conventionally known for melt polycondensation reactions.

Specifically, in a first stage reaction, the organic dihydroxy compound and the carbonic diester are reacted at from about 80 to about 250° C., or preferably from about 100 to about 230° C., with the temperature range of from about 120 to about 190° C. being particularly preferred, for a period of from about 0 to about 5 hours, or preferably, from about 0 to about 4 hours, with the period of from about 0 to about 3 hours being particularly preferred, under normal pressure. Next, the reaction temperature is increased while maintaining the reaction system at reduced pressure, the aromatic dihydroxy compound and carbonic diester are reacted, and finally, melt polycondensation of the aromatic dihydroxy compound and the carbonic diester is carried out at reduced pressure of about 5 mmHg or less, and preferably about 1 mmHg or less, at a temperature of from about 240 to about 320° C.

The polycondensation reaction described above may be carried out continuously or according to the batch method. Moreover, the reaction equipment used in carrying out the above reaction may be of the tank type, the tube type, or the tower type.

By means of the present invention, one can manufacture polycarbonate containing either no μm-sized fine particles or only a minute amount thereof which is well-suited for use as an optical material, particularly as a raw material for optical disk molding.

Various other components may be added as desired to this polycarbonate as additives. Such components may be widely used, with examples including acidic compounds, water, and other additives commonly added to polycarbonate depending on the purpose of use, including thermal stabilizers, epoxy compounds, ultraviolet absorbers, mold-releasing agents, colorants, antistatic agents, slipping agents, antiblocking agents, lubricants, defogging agents, natural oils, synthetic oils, waxes, organic fillers, and inorganic fillers, and these substances may also be used in combinations of two or more.

As the aforementioned acidic compound, one may use sulfur-containing acidic compounds having a pKa value of about 3 or less or derivatives formed from such acidic compounds, with specific examples including sulfurous acid, sulfuric acid, sulfinic acid compounds, sulfonic acid compounds, and derivatives thereof. Among these acidic compounds, substances such as methyl p-toluene sulfonate, ethyl p-toluene sulfonate, and butyl p-toluene sulfonate are particularly preferred.

One may also add the above other components to pelletized polycarbonate and melt-knead the polycarbonate and the additives, or add them to molten polycarbonate prior to pelletization obtained as a reaction product. Two or more of these components may be added simultaneously, or they may be added individually, and they may be added as appropriate at any desired stage.

According to the present invention, which includes the simplified filtration process described above, one can efficiently obtain phenols which either do not contain μm-sized organic or inorganic particulate impurities or contain such impurities only in minute amounts. Such bisphenols are well-suited for use as raw materials for the manufacture of polymers such as polycarbonate, epoxy resin, and polyarylate.

As the polycarbonate obtained according to the present invention shows outstanding properties such as transparency, color tone, heat resistance, and water resistance, and does not contain particulate impurities which give rise to optical scattering, or contains such impurities only in minute amounts, it can be optimally used not only in general molding materials, but in construction materials such as sheets, optical lens materials such as headlight lenses for automobiles and glasses, and optical recording materials, but it is particularly well-suited for use as a molding material for optical disks.

EXAMPLES

The following is an specific explanation of the present invention by means of examples, but the invention is not limited to these examples.

In this specification, the number of fine particles in the bisphenol A manufactured in the examples, the number of fine particles in the polycarbonate, and the MFR of the polycarbonate were measured as follows.

Measurement of Number of Fine Particles

After the bisphenol A was diluted with methanol filtered with a 0.2 μm membrane filter, the number of fine particles measuring 0.5–1.0 μm in diameter was measured using a particle meter (KL-20, manufactured by Rion Co.). The results were expressed as the number of particles per gram of bisphenol A.

The number of particles in the polycarbonate was measured in the same manner as for bisphenol A, except that the diluent solvent used was chloroform rather than methanol.

Example 1

Manufacturing Process of Bisphenol A (a) Phenol and acetone were reacted at a molar ratio of phenol/acetone=5 at 50° C. and ordinary pressure using a sulfonic acid-type cation-exchange resin with a degree of crosslinking of 4% as an acidic catalyst to obtain a mixed solution.

(b) The reaction solution obtained above was vacuum-distilled at 200 mmHg and 120° C., and the unreacted acetone, byproduct water, etc., were removed to obtain a crude solution (bisphenol A).

(c) The phenol was removed from the crude solution obtained above, and the concentration of bisphenol A was adjusted to 30% by weight.

(d) The crude solution having its concentration adjusted as described above (homogeneous solution) was subjected to heat extraction using an external heat exchanger and cooled to 42° C., and an addition compound of bisphenol A and phenol was crystallized, forming a slurry.

(e) The slurry was separated into an addition compound (crystalline portion) and the mother liquor by centrifugation and vacuum filtration.

(f) After being subjected to solid-liquid separation, the addition compound of bisphenol A and phenol was heated and melted at 130° C.

(g) The mixed solution obtained as described above (molten mixture) was vacuum-distilled at 100 mmHg and 190° C. to remove the phenol, and purified liquid bisphenol A was recovered.

(h) The purified bisphenol A obtained as described above was then pelletized.

Filtration of Bisphenol A

The bisphenol A pelletized in process (h) above was melted at 185° C. and filtered as follows using the filtration device shown in FIG. 2.

An SUS 316 calcined metal filter having a filtration grade of 0.2 μm (Porous Filter manufactured by Mott Co.) was installed in the filter housing 7.

First, the process liquid supply valve 4, the filtrate discharge valve 10, and the air vent valve 11 were opened, foreign matter was discharged through washed-out foreign matter disposal line 5, the valve 6 and the backwash solvent supply valve 9 were then closed, phenol was pumped by pump 3 at 80° C. from the raw material tank 2 through valve 4, and the system was thoroughly washed.

Next, the above-mentioned particulate bisphenol A was fed from the raw material supply line 1 to the raw material tank 2, it was heated and melted in the raw material tank 2 at 185° C., and molten bisphenol A was pumped through valve 4 and the filter in filter housing 7 by the pump 3 and discharged through the bisphenol discharge line 12 via the valve 10.

The molten bisphenol A was then caused to flow through the filter at a flow volume of 0.3 gallons/min. per ft$^2$ of the filter.

The number of fine particles in the bisphenol A discharged from the line 12 was then measured. The results are shown in Table 1.

The molten bisphenol A was continuously fed through the raw material supply line 1 to the raw material tank 2 and pumped by pump 3 through valve 4 to the filter in filter housing 7 from the raw material tank 2 and the differential pressure of the outlet filter on the side of the valve 10 was measured. The results showed a measured increase in differential pressure 5 days after the beginning of bisphenol A supply, and as shown in Table 1, it was possible to remove the fine particles in the bisphenol A during this time.

Polycarbonate Manufacturing Process

Bisphenol A filtered as described above (supply rate 36.0 kg/hr) and molten diphenylcarbonate supplied via a direct line after distillation (supply rate 34.7 kg/hr) were continuously supplied to a stirring tank for raw material mixing maintained at the temperatures shown below, $1 \times 10^{-6}$ moles/mol of BPA of sodium hydroxide was added as a catalyst, and polycarbonate was manufactured with a target MFR of 11.0 g/10 min.

The polycarbonate polymerization unit was equipped with one stirring tank for mixing of raw materials, two prepolymerization tanks, and two lateral polymerization tanks, with successive supply to prepolymerization tank I, prepolymerization tank II, lateral polymerization I, and lateral polymerization tank II at a supply rate of 36.0 kg/hr on a bisphenol A basis, and polymerization was carried out under the following conditions.

| Reactor | Pressure | Temperature (°C.) | Average retention time (hrs) |
|---|---|---|---|
| Stirring tank | Nitrogen atmosphere | 160 | 2.0 |
| Prepolymerization tank I | 100 torr | 230 | 1.0 |
| Prepolymerization tank II | 20 torr | 240 | 0.5 |
| Lateral polymerization tank I | 3 ~ 5 torr | 270 | 0.5 |
| Lateral polymerization tank II | 0.1 ~ 1.0 torr | 275 | 0.5 |

While monitoring the measured MFR at 2-hour intervals, the pressure of lateral polymerization tank I and lateral polymerization tank II was monitored so as to operate with as little deviation as possible from the target MFR.

The number of fine particles contained in the polycarbonate manufactured as described above is shown in Table 1.

Example 2

Backwashing of the filter used in Example 1 was carried out.

Figure 2:
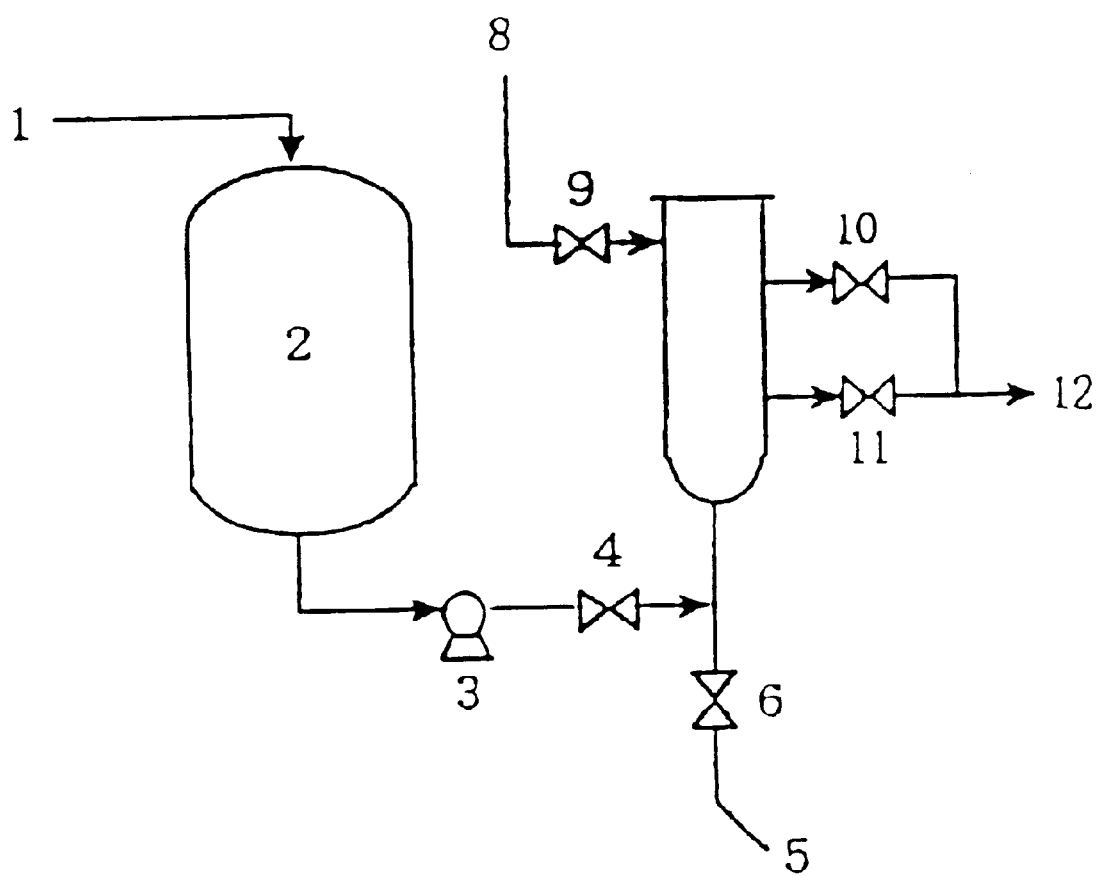
FIG. 2 is a schematic diagram of a filtration device for bisphenol used in the present invention.

In FIG. 2, after the supply of bisphenol A from line 1 was stopped, valves 4, 10, and 11 were shut, and valves 6 and 9 were opened.

Distillation-purified phenol was discharged from backwashing solvent (phenol) supply line 8, and the foreign matter trapped by the filter was removed from line 5.

After backwashing, the same filtration operation as in Example 1 was carried out. In the same manner as Example 1, the number of fine particles in the bisphenol A was measured, and the differential pressure of the outlet filter was measured. The results indicated that after backwashing, the filter showed performance virtually equivalent to that of a new filter. The results are shown in Table 1.

Example 3

Backwashing of the filter used in Example 1 and reusing of the regenerated filter were repeated six times (over a period of approximately one month), and the number of fine particles in the bisphenol A was then measured in the same manner as in Example 1. The results showed that even after backwashing six times, there was no marked decrease in filter performance. These results are shown in Table 1.

Comparison Example 1

The same procedure as in Example 1 was used, except that a PTFE membrane filter having a filtration grade of 0.2 μm (manufactured by Nihon Memtech Co.) was used instead of a calcined metal filter.

The number of fine particles in the bisphenol A was measured in the same manner as in Example 1, and the differential pressure of the outlet filter was measured. The results showed that the particle-removing performance of this filter was identical to that of a calcined metal filter, but due to a sharp elevation of differential pressure 5 days after the supply of bisphenol A was begun, filtration was stopped. The results are shown in Table 1.

Comparison Example 2

Backwashing of the filter used in Comparison Example 1 was attempted in the same manner as in Example 2, but the filter failed.

Comparison Example 3

The number of fine particles in the unfiltered bisphenol A of Example 1 was measured. The results are shown in Table 1.

| | Filter | (Material - Filtration grade) Number of 0.5–1.0 μm fine particles in bisphenol A (particles/g-BPA) | Filter life | Number of fine particles measuring 0.5–1.0 μm in polycarbonate (particles/g-BPA) |
|---|---|---|---|---|
| Example 1 | 1SUS 316 calcined metal filter | 0.2 μm | 1420 | 5 | 1640 |
| Example) 2 | Same as above (after backwashing and regeneration | 0.2 μm | 1530 | 5 | 1710 |

-continued

| | Filter | (Material - Filtration grade) Number of 0.5–1.0 μm fine particles in bisphenol A (particles/g-BPA) | Filter life | Number of fine particles measuring 0.5–1.0 μm in polycarbonate (particles/g-BPA) |
|---|---|---|---|---|
| Example 3 | Same as above (after backwashing/regeneration 6 times) | 0.2 μm 2210 | 4 | 2360 |
| Comparison Example 1 | PTFE membrane filter | 0.2 μm 1340 | 5 | 1520 |
| Comparison Example 2 | Same as above (after backwashing) Could not be used due to failure | 0.2 μm | — | — |
| Comparison Example 3 | Not filtered | 18000 | — | 19600 |

We claim:

1. A manufacturing method for a bisphenol comprising reacting a phenol and a ketone to form bisphenol in a solution or a mixed solution of said bisphenol and phenol, and filtering the solution through a calcined metal filter.

2. An improved method for manufacturing bisphenol pellets wherein purified liquid bisphenol is cooled and made into pellets comprising:
    (a) reacting a phenol and a ketone in the presence of an acidic catalyst to form a reaction mixture comprising liquid bisphenol, catalyst and low-boiling-point substances,
    (b) removing catalyst and low-boiling-point substances from the reaction mixture containing the liquid bisphenol formed,
    (c) obtaining a homogeneous solution of bisphenol with an adjusted concentration by adding or removing a phenol,
    (d) cooling the homogeneous solution and crystallizing an addition compound of a bisphenol and a phenol from the solution to form a slurry,
    (e) subjecting the slurry to solid-liquid separation to obtain from the slurry the addition compound of a bisphenol and a phenol in the form of a solid,
    (f) heating and melting the solid addition compound to obtain a mixed solution,
    (g) removing the phenol from the mixed solution to obtain the purified liquid bisphenol
    wherein the improvement consists of filtering the liquid bisphenol obtained in (a), the homogeneous solution obtained in (c), the mixed solution obtained in (f), or the purified liquid bisphenol obtained in (g) through a calcined metal filter.

3. The improved method for manufacturing bisphenol of claim 2 wherein the mixed solution obtained in (f) or the purified liquid bisphenol obtained in (g) are filtered.

4. The improved method for manufacturing bisphenol of claim 2 wherein (h) the purified liquid bisphenol obtained in (g) is pelletized.

5. The improved method of claim 4, wherein the mixed solution of bisphenol and phenol obtained in (f), the purified liquid bisphenol obtained in (g), or the molten bisphenol in (h) are filtered.

6. The method of claim 1 wherein the filtration grade of the calcined metal filter is 1.0 μm or less.

7. The method of claim 1 wherein, after filtering, the calcined metal filter is backwashed or chemically washed and then reused.

8. The method of claim 1 wherein the bisphenol is bisphenol A.

9. A method for manufacturing polycarbonate wherein bisphenol A obtained by reacting phenol and acetone to form bisphenol A in a solution or a mixed solution of bisphenol A and phenol, and filtering the solution through a calcined metal filter is reacted with diphenylcarbonate by the melt process.

10. The method of claim 9 wherein the filtration grade of the calcined metal filter is 1.0 μm or less.

11. The method of claim 9 wherein, after filtering, the calcined metal filter is backwashed or chemically washed and then reused.

12. A method for manufacturing polycarbonate wherein bisphenol A pellets obtained by reacting phenol and acetone to form bisphenol A by an improved method for manufacturing bisphenol A wherein purified liquid bisphenol A is cooled and made into pellets comprising:
    (a) reacting phenol and acetone in the presence of an acidic catalyst to form a reaction mixture comprising liquid bisphenol A, catalyst and low-boiling-point substances,
    (b) removing catalyst and low-boiling-point substances from the reaction mixture containing the liquid bisphenol A formed,
    (c) obtaining a homogeneous solution of bisphenol A with an adjusted concentration by adding or removing phenol,
    (d) cooling the homogeneous solution and crystallizing an addition compound of bisphenol A and phenol from the solution to form a slurry,
    (e) subjecting the slurry to solid-liquid separation to obtain from the slurry the addition compound of bisphenol A and phenol in the form of a solid,
    (f) heating and melting the solid addition compound to obtain a mixed solution,
    (g) removing the phenol from the mixed solution to obtain the purified liquid bisphenol A
    wherein the improvement consists of filtering the liquid bisphenol A obtained in (a), the homogeneous solution obtained in (c), the mixed solution obtained in (f), or the purified liquid bisphenol obtained in (g) through a calcined metal filter.

13. The improved method for manufacturing bisphenol of claim 12 wherein the mixed solution obtained in (f) or the purified liquid bisphenol obtained in (g) are filtered.

14. The improved method for manufacturing bisphenol of claim 12 wherein (h) the purified liquid bisphenol obtained in (g) is pelletized.

15. The improved method of claim 14, wherein the mixed solution of bisphenol and phenol obtained in (f), the purified liquid bisphenol obtained in (g), or the molten bisphenol in (h) are filtered.

* * * * *

UNITED STATES PATENT AND TRADEMARK OFFICE
CERTIFICATE OF CORRECTION

PATENT NO.: 6,008,315

DATED: December 28, 1999

INVENTOR(S): Takato Kimura, Satoshi Omori,

Ryozo Sato, Tomoaki Shimoda

It is certified that an error appears in the above-identified patent and that said Letters Patent are hereby corrected as shown below:

On the title page of the patent, the Inventors, please correct the spelling of the second named inventor to:

"Satoshi Omori" to the [75] Inventors.

Signed and Sealed this

Twenty-second Day of May, 2001

*Attest:*

NICHOLAS P. GODICI

*Attesting Officer*   *Acting Director of the United States Patent and Trademark Office*